United States Patent [19]
Franceschini et al.

[11] Patent Number: 6,165,441
[45] Date of Patent: *Dec. 26, 2000

[54] METHOD OF DIAGNOSIS AND PHOTODYNAMIC THERAPY OF TUMOURS

[75] Inventors: Rodolfo Franceschini, Saluggia; Giulio Iori, Padua; Laura Polo, Mestre; Giovanni Bocchiotti, Turin, all of Italy

[73] Assignee: Nycomed Amersham Sorin SRL, Milan, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/518,808

[22] Filed: Aug. 24, 1995

[51] Int. Cl.$^7$ ............................. A61K 51/04; A61K 51/12
[52] U.S. Cl. ..................... 424/1.65; 424/1.21; 424/1.85
[58] Field of Search ................................. 424/1.21, 1.11, 424/1.65, 1.69, 450, 1.85; 422/52; 600/1, 3

[56] References Cited

U.S. PATENT DOCUMENTS 5,346,670  9/1994  Renzoni et al. ..................... 422/52

OTHER PUBLICATIONS

Spectroscopic Studies on Zn(II)–Phthalocyanine on Homogeneous and Microheterogeneous System—G Valduga, E. Reddi and G. Jori. Journal of Inorganic Biochemistry, vol. 29, No. 1, pp. 59–65, 1987.

Iodine–131 Labeled Zn(II)–Phthalocyanine: A Potential Therapeutic Agent for Solid Tumours—R. Franceschini et al., European Journal of Nuclear Medicine, vol. 21, No. 8, p. 877. Aug. 21–24, 1994. [Abstract No. 611].

$^{131}$I–Zn(II)–Phthalocyanine: A Potential Radiotracer for Solid Tumours. Franceschini, R. et al., Symposium on Tumour Targeting with Radio Labelled Hormones and Antibodies. Dec. 9–10, 1994. Nuremberg, Germany.

Preparation of $^{131}$I–Label–Zn(II)–Phthalocyanine—R. Franceschini et.al. Appl. Radiol. Isot., Vo. 45, No. 3, pp. 385–403, 1994.

Lenaerts et al., "Nanocapsules with a reduced liver uptake: Targeting of Phthalocyanines to EMT–6 Mouse Mammary Tumour in Vivo", Eur. J. Pharm. Biopharm, 41(1) 1995, pp. 38–43.

Rousseau et al., "Biodistribution and Tumor Uptake of [Ga–67] Chlorogallium–tetraoctadecyloxy Phthalocyanine and its sulfonation Products in Tumor Bearing C–3H Mice," Nucl. Med. Biol., vol. 18, No. 7, pp. 777–782, 1991.

Valduga et al., "Spectroscopic Studies on Zn(II) Phthalocyanine in Homogeneous and Microheterogeneous Systems", Journal of Inorganic Biochemistry, 29, pp. 59–65, 1987.

Scasnar et al., "Biological Activities of Phthalocyanines–XV." Nucl. Med. Biol. vol. 20, No. 3, pp. 257–263, 1993.

*Primary Examiner*—José G. Dees
*Assistant Examiner*—Michael G. Hartley
*Attorney, Agent, or Firm*—Margaret B. Kelley; Clifford Chance Rogers & Wells, LLP

[57] ABSTRACT

A method of therapeutical treatment of tumors, by photodynamic therapy comprising administering to a subject in need of said treatment an effective amount of a tumor-localizing photosensitizer consisting of a metal phthalocyanine, together with a minor amount of a tracer consisting of said metal phthalocyanine labelled with a radioactive isotope and non-invasively monitoring the concentration of said tracer in the target tumoral tissue and in the peritumoral tissue, thereby to identify the appropriate post-administration interval for performing the photodynamic therapy.

10 Claims, 3 Drawing Sheets

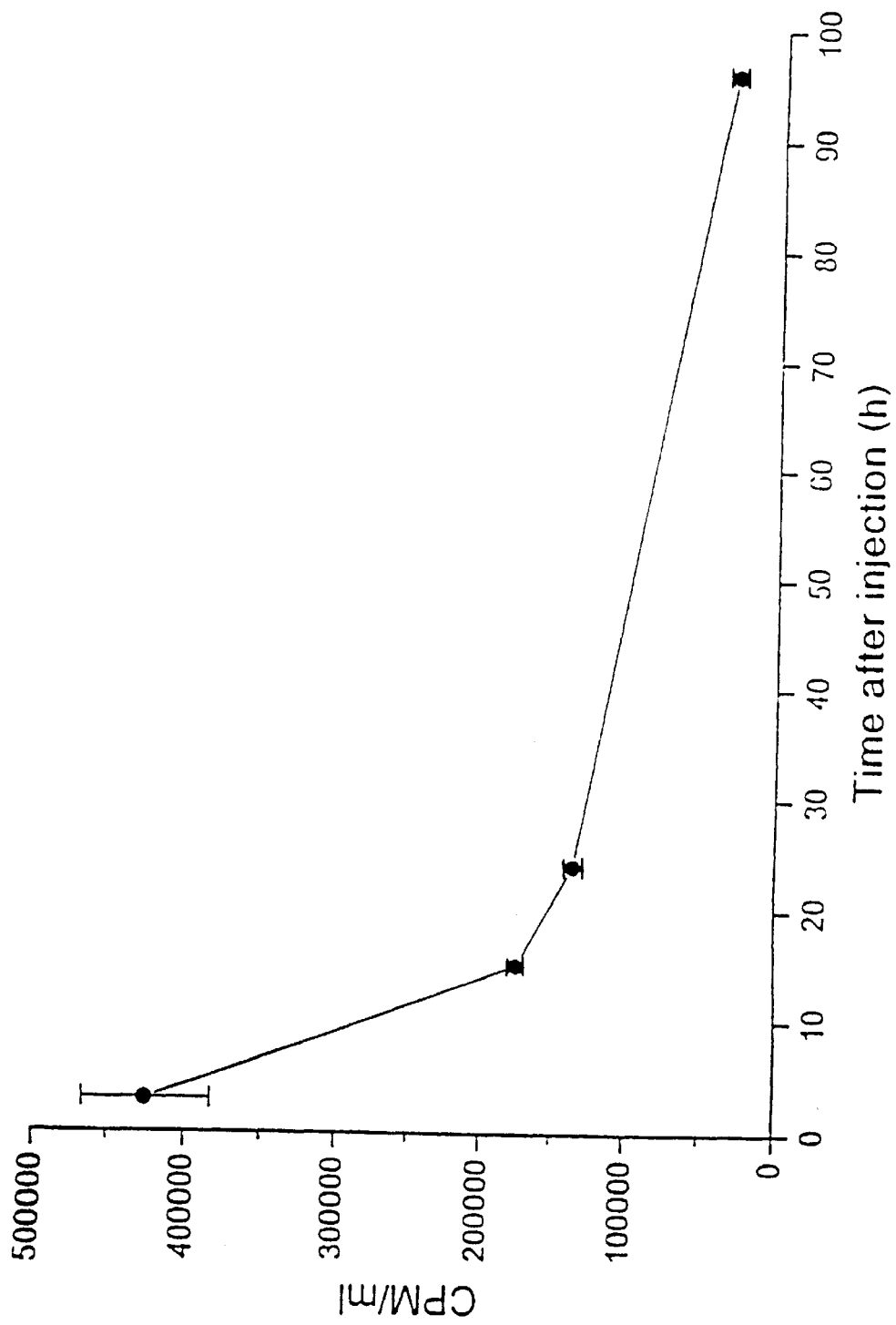
FIGURE 1. Effect of time on the clearance of $^{131}I$-ZnPc from serum of Balb/c mice bearing a MS-2 fibrosarcoma. The mice were injected in the tail vein with 0.096 MBq/g $^{131}I$-ZnPc (0.43mg/kg). Average of at least 3 independently analyzed mice at each time.

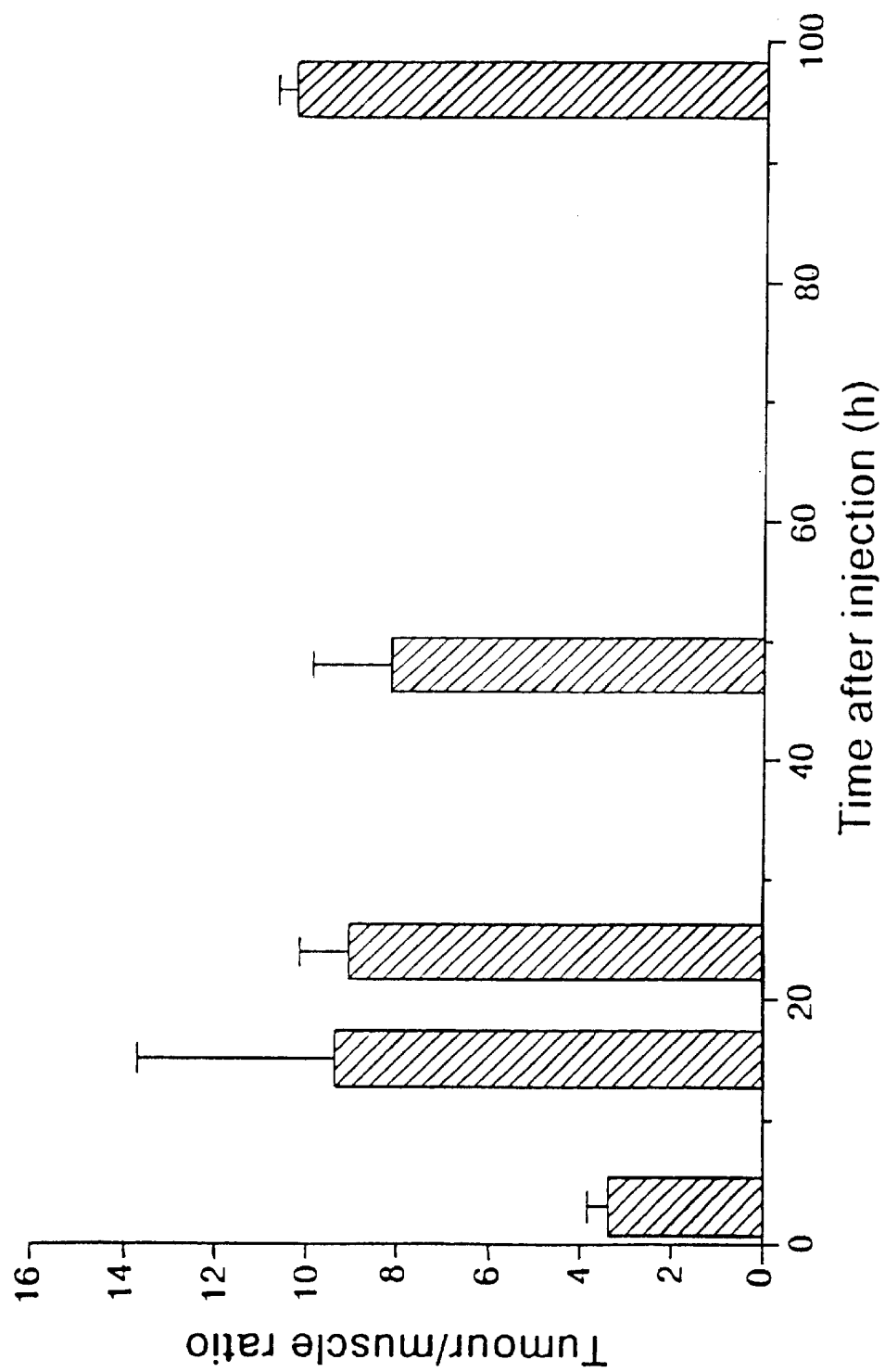
FIGURE 2. Ratio between the tumour/muscle radioactivity of $^{131}$I-ZnPc at different times after injection of 0.096 MBq/g $^{131}$I-ZnPc in DPPC liposomes. Averaged ratios for 3 independently analyzed mice ± s.d.

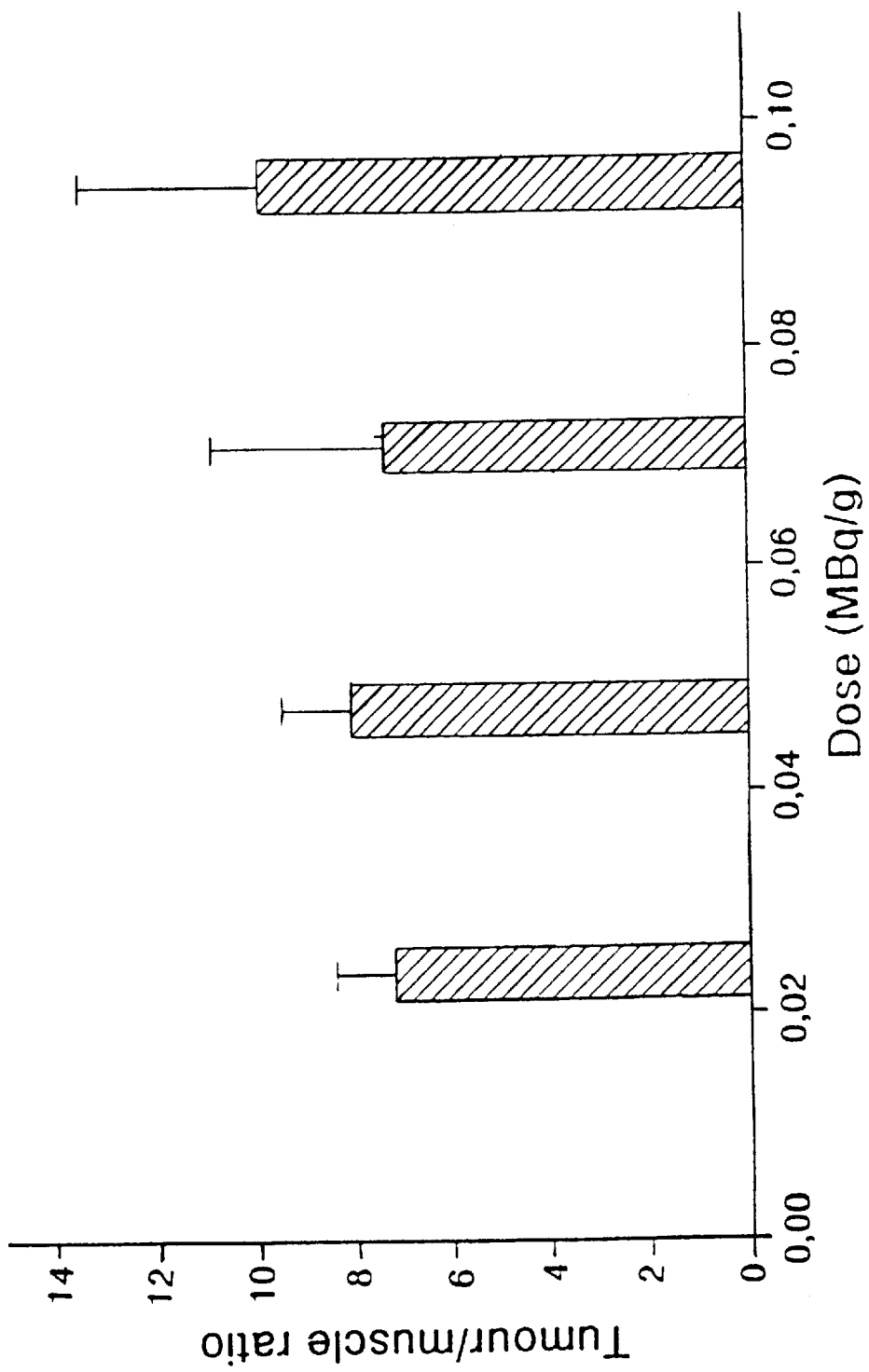
FIGURE 3. Ratio between the tumour/muscle radioactivity of $^{131}$I-ZnPc at different concentration at 24 h after injection of $^{131}$I-ZnPc in DPPC liposomes. Averaged ratios for 3 independently analyzed mice ± s.d.

METHOD OF DIAGNOSIS AND PHOTODYNAMIC THERAPY OF TUMOURS

DESCRIPTION

The present invention relates to a method of diagnosis of tumours and to the therapeutical treatment of solid tumours by photodynamic therapy.

Photodynamic therapy of tumours (PDT) is a modality for the treatment of solid tumours which is based on the use of tumour-localizing photosensitizers and irradiation of the tumour with visible light.

At the clinical level, this technique is most frequently applied using haematoporphyrin (HpD) or its derivatives. However, there is now general agreement that these porphyrins are not ideal photosensitizers.

Photosensitizers, such as phthalocyanines (PC) or their metal derivatives, are being studied in vitro and in vivo as possible candidates for replacing HpD in PDT. Phthalocyanines are heterocyclic compounds consisting of four benzoisoindole rings linked together via nitrogen bridges. They are known to form stable and non-toxic complexes with many metals and certain metal oxides. These metal-PC complexes are readily prepared by condensation of phthalic acids with bivalent cations or by exchange of a metal ion with the central ion of Li- or $H_2$-PC. Phthalocyanines are characterized by strong light absorption in the 670–690 nm region and are accumulated and retained by experimental tumours, especially those of the central nervous system.

Biodistribution and tumour-photosensitizing studies with liposome-incorporated Zn(II)-phthalocyanine pointed out that this compound is phototherapeutically active at doses as low as 0.15 mg/kg body wt. with an enhanced selectivity of tumour accumulation.

An effective photodynamic therapy is however made difficult due to uncertainties in the individual variability of the photosensitizer biodistribution.

A first object of the present invention is to provide an improved method for tumour treatment by photodynamic therapy, which allows for a real-time non-invasive monitoring of the metal phthalocyanine concentration in the tumour and peritumoral tissue, thereby allowing to identify the most convenient post-injection interval for performing the PDT treatment.

Accordingly, the present invention provides a method of therapeutical treatment of tumours by photodynamic therapy comprising administering to a subject in need of said treatment an effective amount of a tumour-localizing photosensitizer consisting of a metal phthalocyanine, together with a minor amount of a tracer consisting of said metal phthalocyanine (MePc) labelled with a radioactive isotope, non-invasively monitoring the concentration of said tracer in the target tumoral tissue and in the peritumoral tissue, thereby to identify the appropriate post-administration interval for performing the PDT treatment.

Since most photosensitizing agents, such as phthalocyanines, are endowed with a significant fluorescence yield, they are suitable candidates for in vivo photodiagnosis of neoplastic lesions. However, in the present state of the development, diagnostic modalities based on fluorescence measurements in vivo present some limitations:
i) the fluorescence quantum yield can be influenced by the aggregation of the photosensitizer in cells or tissues;
ii) the microenvironment of the dye can also affect the fluorescence properties;
iii) several experimental artifacts can induce false positives or negatives.

In principle, these limitations could be overcome at least in part by the use of radiolabelled photosensitizers, since radiodiagnostic measurements are much less sensitive to the aggregation of the dye and the nature of the microenvironment.

The experimental results obtained by the present inventors confirm that metal phthalocyanines, labelled with a radioactive isotope, constitute an effective radiodiagnostic agent for tumours. Accordingly, the present invention also provides a method of early diagnosis of tumours comprising administering to a subject, suspected to be affected by tumour, an amount of a metal phthalocyanine labelled with a radioactive isotope, the administered amount being effective for radiodiagnostic measurements of the labelled metal phthalocyanine on the target tumoral tissue.

Metal phthalocyanines for use according to the invention preferably comprise phthalocyanines, wherein Me is selected from the group consisting of Zn, Ga and In. The radioactive isotope which is used for labelling the MePc is preferably selected from the group consisting $^{131}$I, $^{111}$In and $^{67}$Ga.

The MePc and the MePc tracer are preferably administered i.v. incorporated into unilamellar liposomes, preferably of DL-α-dipalmitoyl-phosphatidylcholine (DPPC).

Experimental Tests

Experimental tests were carried out in Balb/c mice affected by a MS-2 fibrosarcoma. This tumour model had been previously used for extensive PDT studies with unlabelled ZnPc.

For tumour implantation $2\times10^5$ cells in 0.2 ml of sterile physiological solution were intramuscularly injected into the right hind leg of female Balb/c mice having a body wt. of 20–22 g. All the experiments were started on the eighth day after tumour implantation, when the external diameter was ca. 0.8 cm and no detectable spontaneous tumour necrosis had generally occurred. When necessary, mice were anesthetized by i.p. injection of Ketalar (150 mg/kg).

Radioiodination of Zn(II)-phthalocyanine

Typically, 0.02 ml of 13.5 nM Na $^{131}$I (185 MBq) in 0.1 M NaOH solution were introduced into a reacti-vial and the water removed by azeotropic distillation under a nitrogen stream. Then, 0.1 mg of Zn(II)-phthalocyanine in 0.1 ml of anhydrous dimethylformamide (DMF) and 0.05 mg of chloramine T were added to the vial and the reaction mixture was heated to 100° C. for 15 minutes. Electrophoretic studies on labelling kinetics show that labelling yields of 60–70% are obtained after 15–20 minutes at 100° C. The labelling reaction was stopped by adding 0.1 mg of $Na_2S_2O_5$ and the product was purified by anion exchange chromatography to remove any unreacted iodine. The $^{131}$I—ZnPc was eluted as a singlet peak: although no specific characterization of the compound was performed, it appears reasonable to assume that the ZnPc was almost exclusively monoiodinated since the phthalocyanine/Na$^{131}$I molar excess in the reaction mixture was about 630.

Preparation of the Injectable Formulation $^{131}$I—Zn(II)-phthalocyanine was incorporated into small unilamellar vesicles of DPPC following the procedure described by Valduga et al., J.Inorg.Biochem. (1987), 25–59.

Before incorporation into the lipid matrix DMF was removed by lyophilization and the residue solubilized in anhydrous pyridine.

For these experiments, liposomes were prepared in 0.9% aqueous NaCl and dialyzed for 3 hours against 250 ml of saline with a change after the first hour. The incorporation yields of $^{131}$I—Zn(II)-phthalocyanine into unilamellar liposomes of DPPC was 30–35%. "Empty" liposomes devoid of ZnPc were prepared by introducing 0.02 ml of Na-$^{131}$I (185 MBq) into a reacti-vial and removing water by azeotropic distillation under a nitrogen stream. The residue was solubilized in anhydrous pyridine and incorporated into small unilamellar vesicles of DPPC.

Pharmacokinetic Studies

Balb/c mice bearing the MS-2 fibrosarcoma were injected in the tail vein with $^{131}$I—ZnPc at does between 0.024 and 0.096 MBq/g. At predetermined times up to 24 hours after injection, the whole body of the mice was scanned with a Gamma Camera General Electric Stargem in order to ensure the radioactivity levels at different anatomical sites. Then, the mice were sacrificed by prolonged exposure to ether vapours; the blood, tumour and selected normal tissues (muscle, skin, lung, liver, spleen, kidney, brain) were rapidly taken. The blood was centrifuged to remove the erythrocytes and the radioactivity in the plasma (100 $\mu$l) was analyzed. Moreover, tissues were washed with physiological solution, weighed, introduced into RIA test tubes and centrifuged for 10 minutes and 2000 g. The radioactivity was collected for 1 minute by a gamma counter (Packard Selektronik Design). A different group of mice was injected as above described, sacrificed at 3 hours, 15 hours, 24 hours, 48 hours and 96 hours after injection (three mice at each time) and the radioactivity in plasma and tissues homogenates was determined.

BRIEF DESCRIPTION OF THE DRAWINGS

FIG. 1 is a diagram showing the effect of time on the clearance of $^{131}$I—ZnPc from serum of Balb/c mice bearing a MS-2 fibrosarcoma; the mice were injected in the tail vein with 0.096 MBq/g $^{131}$I—ZnPc (0.43 mg/kg); the data are the average of at least three independently analyzed mice at each time.

FIG. 2 is an histogram showing the ratio between the tumour/muscle radioactivity of $^{131}$I—ZnPc at different times after injection of 0.096 MBq/g $^{131}$I—ZnPc in DPPC liposomes; averaged ratios for three independently analyzed mice±s.d..

FIG. 3 is an histogram showing the ratio between the tumour/muscle radioactivity of $^{131}$I—ZnPc at different concentrations at 24 hours after injection of $^{131}$I—ZnPc in DPPC liposomes; averaged ratio for three independently analyzed mice±s.d..

RESULTS

The pharmacokinetic behaviour of i.v. injected $^{131}$I—ZnPc (0.096 MBq/g) incorporated into unilamellar liposomes of DPPC was examined. As shown in FIG. 1, $^{131}$I—ZnPc is almost completely eliminated from mouse serum within 96 hours; the clearance rate is particularly fast during the initial 15 hours after administration. The time dependence of $^{131}$I—ZnPc distribution in tumour and selected normal tissues is shown in Table 1.

The recovery of $^{131}$I—ZnPc is very high in the liver and spleen as expected, since the components of the reticuloendothelial system exhibit a high affinity for systemically injected lipid-type particles. Moreover, hydrophobic photosensitizers are largely eliminated from the organism via the bile-gut pathway. This conclusion is confirmed by the comparatively low levels observed in kidneys. On the other hand, minimal amounts of $^{131}$I—ZnPc are recovered from brain, hence any toxic effects of the drug on the central nervous system are unlikely.

The most important pharmacokinetic parameter is represented by the difference in $^{131}$I—ZnPc concentration between tumour and muscle, which is the peritumoral tissue in the animal model, thus indicating the level of selectivity of tumour targeting. While in tumour the maximum accumulation is observed at 24 hours, small amounts of phthalocyanine are recovered from muscle at all times (Table 1). The tumour-to-muscle concentration ratio is shown in the histograms in FIG. 2. The maximum ratio is obtained at 15 hours after administration and remains at an essentially constant level throughout the studied time interval.

Similar experiments were performed as a function of $^{131}$I—ZnPc dose, as shown in FIG. 3. The tumour/muscle ratio of phthalocyanine concentration at 24 hours after administration is affected to a minor extent by the injected dose. The pharmacokinetic results obtained with empty liposomes show a time-dependent pattern of $^{131}$I radioactivity similar with that observed for the phthalocyanine, namely an increase of the tumour/muscle ratio up to 24 hours.

The obtained data clearly indicate that $^{131}$I-labelled ZnPc is an efficient and selective tumour localizer; the same properties are to be expected for ZnPc labelled with $^{67}$Ga and $^{111}$In.

The pharmacokinetic properties of this phthalocyanine show several similarities with those previously defined for the parent molecule ZnPc in the same animal model. Such analogies include:

a) the apparently polyphasic clearance from the serum with almost 80% of the initial radioactivity disappearing within the initial 24 hours post-injection;

b) the relatively low rate of uptake by the tumour as compared with several normal tissues, with maximal concentration reached after ca. 24 hours;

c) the large amount accumulated by liver and spleen, which is followed by a relatively slow elimination at least during the initial four days; this suggests that the most important mechanism for $^{131}$I—ZnPc elimination from the organism occurs via the bile-gut pathway with only minor amounts cleared via the kidneys.

The main differences between $^{131}$I—ZnPc and ZnPc are represented by the greater accumulation of the former phthalocyanine in the liver at short post-injection times (ca. 7-fold larger concentration than in the tumour) and, most of all, by its almost twice higher selectivity of tumour targeting, as shown by the tumour/muscle ratios of phthalocyanine recovery.

The in vivo analysis of the radioactivity distribution in the whole animals shows that at all examined time intervals the radioactivity is strictly localized at the level of liver and tumour with no general delocalization throughout the organism; hence, it is unlikely that $^{131}$I is dissociated from the phthalocyanine to any significant extent.

Since metal phthalocyanines have been repeatedly observed to be an efficient tumour-targeting dye, the experimental data strongly support the possibility of using metal phthalocyanines, labelled with a radioactive isotope, such as $^{131}$I, $^{67}$Ga and $^{111}$In as a radiodiagnostic agents for tumour, which could overcome at least some of the drawbacks associated with the fluorescence diagnostic technique.

Moreover, since the kinetics of tumour uptake and clearance are quite similar for $^{131}$I—ZnPc and ZnPc, the data confirm the possibility of using the radiolabelled derivative for a real-time non-invasive monitoring of the metal phthalocyanine concentration in the tumour and peritumoral tissue, in order to identify the most convenient post-injection interval for performing the PDT treatment.

TABLE 1

Recoveries (CPM/mg of tissue) of ZnPc-$^{131}$I from tissues of tumour-bearing mice at different times after injection of 0.096 MBq/g ZnPc-$^{131}$I in DPPC liposomes
Average of three independently analyzed mice ± s.d.

| TISSUE | TIME | | | | |
|---|---|---|---|---|---|
| | 3 h | 15 h | 24 h | 48 h | 96 h |
| LIVER | 984.2 ± 15.7 | 871.1 ± 146.8 | 1043.7 ± 72.5 | 849.1 ± 90.3 | 831.9 ± 52.5 |
| SPLEEN | 600.9 ± 8.1 | 503.7 ± 46.8 | 635.1 ± 65.8 | 549.7 ± 96.2 | 413.0 ± 42.7 |
| KIDNEY | 156.9 ± 9.7 | 84.4 ± 8.4 | 77.3 ± 11.2 | 59.4 ± 7.5 | 61.6 ± 16.8 |
| TUMOUR | 140.3 ± 38.6 | 182.7 ± 16.0 | 212.9 ± 8.6 | 180.7 ± 31.4 | 162.2 ± 19.5 |
| MUSCLE | 41.1 ± 3.6 | 22.4 ± 9.3 | 23.7 ± 2.0 | 22.3 ± 0.9 | 15.8 ± 2.5 |
| LUNG | 168.3 ± 5.6 | 76.2 ± 31.4 | 83.3 ± 12.4 | 73.4 ± 9.9 | 52.1 ± 6.9 |
| BRAIN | 11.7 ± 0.1 | 5.2 ± 1.5 | 4.3 ± 0.6 | 3.4 ± 0.7 | 2.0 ± 0.4 |

What is claimed is:

1. A method of treating a target tumor in a human subject, which comprises the steps of:
    (a) co-administering to the individual human subject an effective amount of a therapeutic mixture consisting of (i) a major amount of a tumor-localizing metal phathalocyanine photosensitizer and ii) a minor amount of a radioactive tracer consisting of the metal phathalocyanine photosensitizer labeled with a radioactive isotope;
    (b) non-invasively monitoring the concentration of the radioactive tracer in tumoral tissue and peritumoral tissue;
    (c) determining the optimal time for beginning irradiation of the target tumor containing the photosensitzer compound; and
    (d) irradiating the target tumor with visible light.

2. A method according to claim 1, wherein the metal in the metal phthalocyanine is selected from the group consisting of Zn, Ga and In.

3. A method according to claim 1, wherein the radioactive isotope is selected from the group consisting of $^{131}$I, $^{67}$Ga and $^{111}$In.

4. A method according to claim 1, wherein the metal phthalocyanine photosensitizer and the radioactively labelled metal phthalocyanine tracer are incorporated into a unilamellar liposome before administration.

5. A method according to claim 4, wherein the liposomes are DL-α-dipalmitoyl-phosphatidylcholine liposomes.

6. A method according to claim 1, wherein the metal phthalocyanine is zinc phthalocyanine and the metal phthalocyanine labelled with the radioactive isotope is $^{131}$I-zinc phthalocyanine.

7. A method according to claim 1, wherein the metal phthalocyanine is selected from the group consisting of Zn, Ga, and In and wherein the radioactive isotope is selected from the group consisting of $^{131}$I, $^{67}$Ga, and $^{111}$In.

8. A method according to claim 4, wherein the metal phthalocyanine is selected from the group consisting of Zn, Ga, and In and wherein the radioactive isotope is selected from the group consisting of $^{131}$I, $^{67}$Ga, and $^{111}$In.

9. A method according to claim 5, wherein the metal phthalocyanine is selected from the group consisting of Zn, Ga, and In and wherein the radioactive isotope is selected from the group consisting of $^{131}$I, $^{67}$Ga, and $^{111}$In.

10. A method according to claim 5, wherein the metal phthalocyanine is zinc phthalocyanine and the metal phthalocyanine labelled with the radioactive isotope is $^{131}$I-zinc phthalocyanine.

* * * * *